United States Patent [19]

Hill

[11] 4,171,360

[45] Oct. 16, 1979

[54] PHOSPHINEGOLD (I) SALTS HAVING ANTIARTHRITIC ACTIVITY

[75] Inventor: David T. Hill, North Wales, Pa.

[73] Assignee: SmithKline Corporation, Philadelphia, Pa.

[21] Appl. No.: 879,319

[22] Filed: Feb. 21, 1978

[51] Int. Cl.$^2$ .................. C07F 1/12; A61K 33/24; A61K 31/44

[52] U.S. Cl. .................................. 424/245; 546/2

[58] Field of Search ............... 260/270 PY; 424/245; 546/2

[56] References Cited

PUBLICATIONS

Jones et al. I, J.C.S. Dalton, 1434 (1977).
Jones et al. II, J.C.S. Dalton, 1440 (1977).

*Primary Examiner*—Mark L. Berch
*Attorney, Agent, or Firm*—Joan S. Keps; Richard D. Foggio; William H. Edgerton

[57] ABSTRACT

The compounds are (pyridine) (trisubstituted phosphine) gold(I) salts which have antiarthritic activity.

4 Claims, No Drawings

PHOSPHINEGOLD (I) SALTS HAVING ANTIARTHRITIC ACTIVITY

This invention relates to new (pyridine) (trisubstituted phosphine) gold (I) salts. These compounds have antiarthritic activity and, in particular, are of use in the treatment of rheumatoid arthritis.

The compounds of this invention are represented by the following formula:

FORMULA I

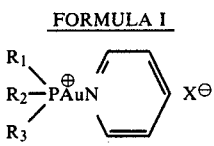

in which:
R₁ is lower alkyl, lower alkoxy or phenyl, said phenyl being optionally substituted by halogen or lower alkoxy;
R₂ and R₃ are lower alkyl or lower alkoxy and
X is a weakly nucleophilic anion.

A particular compound of this invention is represented by Formula I in which $R_1$, $R_2$ and $R_3$ are each ethyl.

The anion X in Formula I is a weakly nucleophilic anion such as, for example, perchlorate ($ClO_4$), iodate ($IO_4$), tetrafluoroborate ($BF_4$) and hexafluorophosphate ($PF_6$).

The compounds of this invention are prepared by the following procedure:

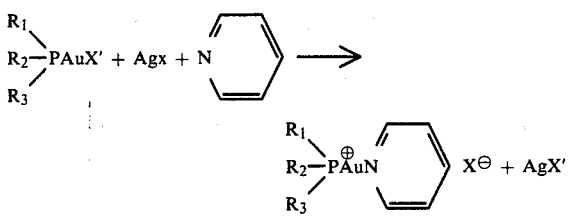

The terms $R_1$, $R_2$, $R_3$ and X are as defined above and X' is halo.

According to the above procedure, a halo (trisubstituted phosphine) gold (I) compound is reacted with a silver salt AgX and pyridine to give the compounds of Formula I. The reaction is carried out in a suitable solvent, such as acetone, conveniently at room temperature.

The halo (trisubstituted phosphine) gold (I) starting materials in the above procedure may be prepared by reacting thiodiglycol with gold acid halide trihydrate to give halo [di(2-hydroxyethyl)-sulfide]gold (I) which is then reacted with a trisubstituted phosphine.

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 mg. of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg. to about 10 mg.

The method of producing antiarthritic activity by administering internally to an animal a compound of Formula I is also an object of this invention. The compounds of Formula I are administered in an amount sufficient to produce antiarthritic activity. The route of administration may be orally or parenterally, preferably orally. Advantageously, doses will be administered 1 to 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

A solution of 2.07 g. (0.01 mole) of silver perchlorate in 30 ml. of acetone was added dropwise to a solution of 3.5 g. (0.01 mole) of chloro(triethylphosphine) gold (I)

and 0.8 ml. of pyridine in 50 ml. of acetone. After stirring 30 minutes, the mixture was filtered and the solvent removed at reduced pressure to give a solid product. Recrystallization from acetone upon the addition of ether to the cloud point and cooling to −78° C. gives (pyridine) (triethylphosphine) gold (I) perchlorate, m.p. 71–73° C.

EXAMPLE 2

In the procedure of Example 1 using in place of chloro(triethylphosphine)gold (I) the following:
chloro(trimethylphosphine)gold (I)
chloro(triisopropylphosphine)gold (I)
chloro(tributylphosphine)gold (I)
the products are:
(pyridine) (trimethylphosphine)gold (I) perchlorate
(pyridine) (triisopropylphosphine)gold (I) perchlorate
(pyridine) (tributylphosphine)gold (I) perchlorate.

EXAMPLE 3

Using silver iodate in the procedure of Example 1 in place of silver perchlorate gives (pyridine) (triethylphosphine)gold (I) iodate.

Similarly, using silver tetrafluoroborate in place of silver perchlorate, the product is (pyridine)(triethylphosphine)gold (I) tetrafluoroborate.

Also, using silver hexafluorophosphate, the product is (pyridine) (triethylphosphine)gold (I) hexafluorophosphate.

EXAMPLE 4

A solution of 14 g. (0.11 mole) of thiodiglycol in 35 ml. of ethanol was added to a solution of 22.1 g. (0.055 mole) of gold acid chloride trihydrate in 105 ml. of distilled water at 0° C. A solution of 10 g. of (diethyl) (phenyl)-phosphine in 35 ml. of ethanol was then added dropwise. After stirring for 30 minutes, the mixture was extracted with chloroform and the chloroform extracts dried, filtered and the solvent removed in vacuo to give an oil. Purification of this oil by dry column chromatography and recrystallization from ether gave chloro[(diethyl) (phenyl)phosphine]gold (I) as white crystalline material having a melting point of 61°–63° C.

Using chloro[(diethyl) (phenyl)phosphine]gold (I) in place of chloro(triethylphosphine)gold (I) in the procedure of Example 1 gives (pyridine)-[(diethyl) (phenyl)-phosphine]gold (I) perchlorate.

EXAMPLE 5

Using in place of (diethyl) (phenyl)-phosphine in the procedure of EXAMPLE 4, the following phosphines:
(dimethyl) (phenyl)phosphine
(dipropyl) (phenyl)phosphine
(dibutyl) (phenyl)phosphine
(diisobutyl) (phenyl)phosphine
(ethyl) (methyl) (phenyl)phosphine
(methyl) (propyl) (phenyl)phosphine
(t-butyl) (methyl) (phenyl)phosphine
the products are:
(pyridine) [(dimethyl) (phenyl)phosphine]-gold (I) perchlorate
(pyridine) [(dipropyl) (phenyl)phosphine]-gold (I) perchlorate
(pyridine) [(dibutyl) (phenyl)phosphine]-gold (I) perchlorate
(pyridine) [(diisobutyl) (phenyl)phosphine]-gold (I) perchlorate
(pyridine) [(ethyl) (methyl) (phenyl)phosphine]-gold (I) perchlorate
(pyridine) [(methyl) (propyl) (phenyl)phosphine]-gold (I) perchlorate
(pyridine) [(t-butyl) (methyl) (phenyl)phosphine]-gold (I) perchlorate.

EXAMPLE 6

A solution of 13.4 g. (0.11 mole) of thiodiglycol in 30 ml. of ethanol was mixed with a solution of 20.0 g. (0.05 mole) of gold acid chloride trihydrate in 90 ml. of distilled water. When the solution was almost colorless, it was cooled to 0° C. and 10 g. (0.05 mole) of (diethoxy) (phenyl)phosphine in 30 ml. of ethanol was added dropwise to the stirred solution. After stirring for one hour, the two phase reaction mixture was extracted with chloroform and the combined chloroform extract was washed with water, dried over magnesium sulfate, filtered and the solvent removed from the filtrate at reduced pressure to give an oil. Chromatography ('Florisil'/chloroform) gave chloro[(diethoxy) (phenyl)phosphine]gold (I) as a colorless oil in the first fraction.

Using chloro[(diethoxy) (phenyl)phosphine]-gold (I) in place of chloro (triethylphosphine)gold (I) in the procedure of Example 1 gives (pyridine)[(diethoxy)-(phenyl)phosphine]gold (I) perchlorate.

EXAMPLE 7

Using (dimethoxy) (phenyl) phosphine in place of (diethoxy) (phenyl)phosphine in the procedure of Example 6 gives, as the product, (pyridine)[(dimethoxy)-(phenyl)phosphine]gold (I) perchlorate.

Similarly, using (p-chlorophenyl) (diethoxy)-phosphine and (p-bromophenyl) (diethoxy)phosphine, the products are (pyridine) [(p-chlorophenyl) (diethoxy)-phosphine]gold (I) perchlorate and (pyridine) [(p-bromophenyl) (diethoxy)phosphine]gold (I) perchlorate.

Also, using (diethoxy) (p-methoxyphenyl)-phosphine in the procedure of Example 6, the product is (pyridine) [(diethoxy) (p-methoxyphenyl)-phosphine]gold (I) perchlorate.

In the same manner, using (phenyl) (dipropoxy)phosphine and (dibutoxy) (phenyl)phosphine, the products are (pyridine) [(phenyl) (dipropoxy)phosphine]gold (I) perchlorate and (pyridine) [(dibutoxy) (phenyl)phosphine]gold (I) perchlorate.

EXAMPLE 8

A solution of 10 g. (0.08 mole) of diethylphosphinous chloride in 100 ml. of ether was added to a solution of p-chlorophenyllithium [prepared from 15.4 g. (0.08 mole) of p-chlorobromobenzene in 100 ml. of ether and 54 ml. of 1.5M n-butyllithium in hexane] under a nitrogen atmosphere. After 30 minutes, the reaction mixture was quenched with a few drops of ethyl acetate and the solvent was removed at reduced pressure. Distillation of the residual oil gave (p-chlorophenyl) (diethyl)phosphine, b.p. 86°–89° C. at 1.5 mm.

A solution of 4.7 g. (0.038 mole) of thiodiglycol in 30 ml. of ethanol was added to a solution of 7.7 g. (0.019 mole) of gold acid chloride trihydrate in 45 ml. of distilled water. The colorless solution was cooled to 0° C. and a solution of 3.9 g. (0.019 mole) of (p-chlorophenyl) (diethyl)phosphine in 15 ml. of ethanol was added. After stirring for 45 minutes, the layers were separated and methylene chloride was added to the organic phase. The resulting solution was washed with distilled water, then dried with sodium sulfate, filtered and the solvent removed in vacuo to give an oily residue. This material was dissolved in ether and an equal volume of low boiling petroleum ether was added. The solid precipitate was filtered off and air dried to give chloro[(p-chlorophenyl) (diethyl)phosphine]gold (I), m.p. 77°–79° C.

By the procedure of Example 1, using chloro[p-chlorophenyl) (diethyl)phosphine]gold (I), the product is (pyridine) [(p-chlorophenyl) (diethyl)phosphine]gold (I) perchlorate.

Using silver iodate in place of silver perchlorate, the product is (pyridine) [(p-chlorophenyl) (diethyl)phosphine]gold (I) iodate.

EXAMPLE 9

A solution of 10 g. (0.08 mole) of diethylphosphinous chloride in 100 ml. of ether was added to a solution of p-methoxyphenyllithium [prepared from 23.4 g. (0.1 mole) of p-iodoanisole in 100 ml. of ether and 62.5 ml. of 1.6 M n-butyllithium in hexane] under a nitrogen atmosphere. After 40 minutes, the reaction mixture was filtered and the solvent removed at reduced pressure. Distillation of the residual oil gave (diethyl) (p-methoxyphenyl)phosphine as a colorless liquid, b.p. 85°–90° C. at 0.5 mm.

A solution of 6.8 g. of thiodiglycol in 40 ml. of ethanol was added to a solution of 11.1 g. of gold acid chloride trihydrate in 60 ml. of distilled water. When the solution became colorless, it was cooled to 0° C. and a solution of 5.5 g. of (diethyl) (p-methoxyphenyl)phosphine in 15 ml. of ethanol was added. After stirring 20 minutes, the reaction mixture was extracted with methylene chloride. The combined methylene chloride extracts were washed with water, dried with sodium sulfate, filtered and the solvent removed at reduced pressure to give a pale gold oil. Purification was accomplished with dry column chromatography (alumina/chloroform) to give chloro[(diethyl) (p-methoxyphenyl)phosphine]gold (I) as a colorless oil.

Using chloro[(diethyl) (p-methoxyphenyl)phosphine]gold (I) in the procedure of Example 1, the product is (pyridine) [(diethyl) (p-methoxyphenyl)phosphine]gold (I) perchlorate.

EXAMPLE 10

Using the following tri-substituted phosphines in place of (diethoxy) (phenyl)phosphine in the procedure of Example 6:
(ethoxy) (methyl) (phenyl)phosphine
(ethoxy) (ethyl) (phenyl)phosphine
(butoxy) (ethoxy) (phenyl)phosphine
(p-chlorophenyl) (ethoxy) (ethyl)phosphine
the following products are obtained, respectively:
(pyridine) [(ethoxy) (methyl) (phenyl)phosphine]gold (I) perchlorate
(pyridine) [(ethoxy) (ethyl) (phenyl)phosphine]gold (I) perchlorate
(pyridine) [(butoxy) (ethoxy) (phenyl)phosphine]gold (I) perchlorate
(pyridine) [(p-chlorophenyl) (ethoxy) (ethyl)phosphine]gold (I) perchlorate.

EXAMPLE 11

Using, in the procedure of Example 4, (p-bromophenyl) (diethyl)phosphine in place of (diethyl)-(phenyl)phosphine, the product is (pyridine) [(p-bromophenyl) (diethyl)phosphine]gold (I) perchlorate.

Similarly, using (p-ethoxyphenyl) (diethyl)-phosphine, the product is (pyridine) [(p-ethoxyphenyl)-(diethyl)phosphine]gold (I) perchlorate.

EXAMPLE 12

| Ingredients | Amounts |
|---|---|
| (pyridine) (triethylphosphine) gold (I) perchlorate | 5 mg. |
| magnesium stearate | 5 mg. |
| lactose | 200 mg. |

The above ingredients are screened, mixed and filled into a hard gelatin capsule.

The capsules are administered orally to subjects in need of antiarthritic treatment in amounts within the daily dose range given hereabove.

Similarly, the other gold compounds of Formula I may be formulated into capsules by the procedure of Example 12.

Other pharmaceutical compositions such as tablets containing a compound of Formula I as the active ingredient are formulated by standard procedures.

What is claimed is:

1. A compound of the formula:

in which:
R$_1$ being alkyl, lower alkoxy or phenyl, said phenyl being optionally monosubstituted by halogen or lower alkoxy;
R$_2$ and R$_3$ are lower alkyl or lower alkoxy and
X is a weakly nucleophilic anion selected from perchlorate, iodate, tetrafluoroborate or hexafluorophosphate.

2. A pharmaceutical composition having antiarthritic activity, in dosage unit form, comprising a pharmaceutical carrier and a compound of claim 1.

3. A compound of claim 1 in which R$_1$, R$_2$ and R$_3$ are each ethyl.

4. A method of producing antiarthritic activity which comprises administering internally to an animal pharmaceutical composition of claim 2.